United States Patent
Ogura et al.

(10) Patent No.: US 6,673,361 B1
(45) Date of Patent: Jan. 6, 2004

(54) POLYMER, IN VIVO DEGRADABLE MATERIAL, AND USE

(75) Inventors: Atsuhiko Ogura, Tsuchiura (JP); Hiroshi Iwasaki, Iruma (JP); Shinji Tanaka, Tsukuba (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 09/980,719

(22) PCT Filed: May 18, 2000

(86) PCT No.: PCT/JP00/03181
§ 371 (c)(1),
(2), (4) Date: Nov. 15, 2001

(87) PCT Pub. No.: WO00/71602
PCT Pub. Date: Nov. 30, 2000

(30) Foreign Application Priority Data

May 19, 1999 (JP) ............................................. 11/139293

(51) Int. Cl.[7] ........................... A61F 2/00; C08F 283/02
(52) U.S. Cl. ....................... 424/423; 525/419; 525/432; 525/434; 525/509; 525/540; 424/422; 424/426; 424/443; 424/457
(58) Field of Search .................................. 525/419, 432, 525/434, 509, 540; 424/422, 423, 426, 443, 457

(56) References Cited

U.S. PATENT DOCUMENTS 4,526,938 A * 7/1985 Churchill et al. ............ 525/154

FOREIGN PATENT DOCUMENTS

| EP | 0397307 A2 | 11/1990 |
|---|---|---|
| JP | 63-132939 | 6/1988 |
| WO | 92/00748 | 1/1992 |
| WO | 92/16555 | 10/1992 |

OTHER PUBLICATIONS

Polymer Journal, vol. 19, No.4, (1987) Kohei Kugo et al., Synthesis and Conformations of A–B–A Tri–block Copolymers with Hydrophobic Poly (g–benzyl L–glutamate) and Hydrophilic Poly (ethylene oxide), pp. 375–381.

Yukihira Hisago et al., "Poly (β–benzil–L–aspartate) wo fukumu ABA gata Block Kyoujugoutai no Gousei to sono Saibou Secchakusei", Koubunshi Ronbunshu, vol. 42, No. 11, (Nov., 1985) pp. 731–738.

* cited by examiner

Primary Examiner—Samuel A. Acquah
(74) Attorney, Agent, or Firm—Darby & Darby

(57) ABSTRACT

A polymer having a satisfactory balance between in vivo degradability and satisfactory mechanical properties, which is an $A^1BA^2$ type polymer comprising a segment $A^1$ and a segment $A^2$ each having a modified amino acid and a segment B consisting of polyethylene glycol with a number-average molecular weight of 8000 or higher bonded at one end to the segment $A^1$ and at the other end to the segment $A^2$, and has a number-average molecular weight of 10000 to 600000; an in vivo degradable material which comprises the polymer; and a film for preventing tissue adhesion, an artificial dura mater, a suture, an implant preparation, or a sustained-release drug base each comprising the degradable material.

10 Claims, 3 Drawing Sheets

POLYMER, IN VIVO DEGRADABLE MATERIAL, AND USE

TECHNICAL FIELD

The present invention relates to polymers such as biodegradable tri-block copolymers and biodegradable materials having desirable mechanical properties. The present invention further relates to membranes for preventing tissue adhesion, artificial dura mater, suture threads, implant preparations, and sustained-release drug bases, using such materials.

BACKGROUND ART

Polymers for a bio-material are required to have a variety of functionalities depending on their applications. Among such functionalities are non-toxicity such as non-pyrogenicity or non-allergenicity, mechanical properties to render the materials compatible with tissues and living bodies, ability to separate substances, and ability to release drugs in a sustained manner.

For example, anti-adhesion membrane for prevention of post surgical adhesion of tissue are required to have properties such as readiness to insert into tissue, non-adhesiveness and low irritancy to tissue, biodegradability for eliminating the need to extirpate the membrane, mechanical strengths and elasticity that result in high followability to follow movements of tissues.

However, the required functionalities are not necessarily provided in a well-balanced manner in conventional bio-materials, and hence, the need exists for novel materials in which these functionalities are well-balanced.

An ABA-type tri-block copolymer has been proposed in which the segment B is polyethylene glycol and the segment As, provided at opposite ends of the unit B, are hydrophobic poly-β-benzyl-L-aspartate (which may be referred to simply as PBLA, hereinafter) or poly-β-benzyl-L-glutamate (which may be referred to simply as PBLA, hereinafter) (*Papers on polymers*, vol. 42, No. 11, 731–738 (1985)).

In any of conventional ABA-type tri-block copolymers, however, the segment B, a polyethylene glycol segment, has a number average molecular weight of 6000 or less. Such tri-block copolymers cannot be used as a biodegradable material since they lack sufficient mechanical strength and degrade at an excessively high rate in vivo.

DISCLOSURE OF THE INVENTION

It is an objective of the present invention to provide copolymers such as tri-block copolymers that have biodegradability and good mechanical properties in a well-balanced manner and to provide biodegradable materials using such copolymers.

Another objective of the present invention is to provide membranes for preventing tissue adhesion, artificial dura mater, suture threads, implant preparations, and matrices for sustained drug release, which have biodegradability and good mechanical properties in a well-balanced manner and have various functionalities as a bio-material.

In an effort to address these objectives, the inventors have found out that polymers, such as tri-block copolymers, of particular molecular weights having a segment with modified hydrophobic amino acids on either end of a hydrophilic polyethylene glycol of a particular molecular weight exhibit a high strength, elasticity, low irritancy, and bioabsorbability, and completed the present invention.

According to the present invention, there is provided an $A^1BA^2$-type polymer having a number average molecular weight of 10000 to 600000, wherein the polymer is composed of a segment $A^1$ and a segment $A^2$ each including modified amino acids, and a segment B composed of polyethylene glycol with a number average molecular weight of 8000 or higher, the segment $A^1$ being bonded to one end of the segment B while the segment $A^2$ is bonded to the other end of the segment B.

According to the present invention, there is further provided a biodegradable material containing the $A^1BA^2$-type polymer.

According to the present invention, there is further provided a membrane for preventing tissue adhesion that is composed of the biodegradable material.

According to the present invention, there is further provided an artificial dura mater composed essentially of the biodegradable material.

According to the present invention, there is further provided a suture thread composed essentially of the biodegradable material.

According to the present invention, there is further provided an implant preparation composed essentially of the biodegradable material.

According to the present invention, there is further provided a sustained release drug base composed essentially of the biodegradable material.

PREFERRED EMBODIMENTS OF THE INVENTION

Figure 1:
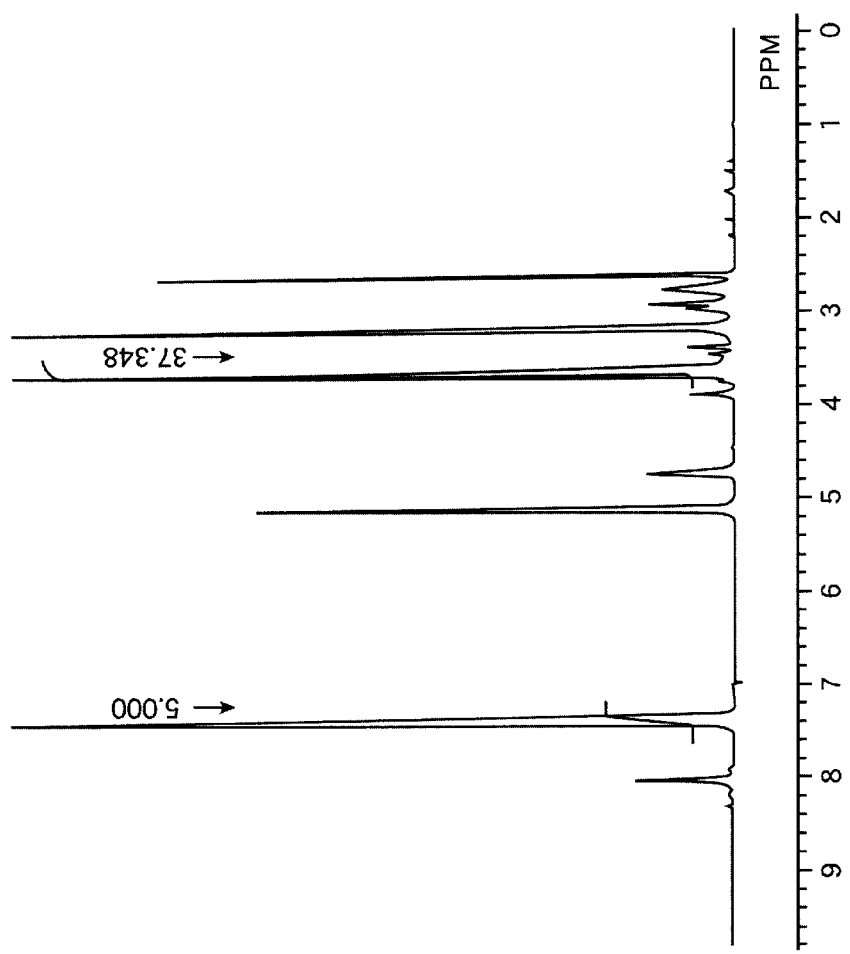
FIG. 1 shows a $^1$H-NMR spectrum of a tri-block copolymer synthesized in Example 1.

The $A^1BA^2$-type polymer of the present invention is a polymer of a particular number average molecular weight which is composed of a segment $A^1$ and a segment $A^2$, each having modified amino acids, and a segment B composed of polyethylene glycol of a particular number average molecular weight. The segment $A^1$ is bonded to one end of the segment B while the segment $A^2$ is bonded to the other end of segment B.

The polymer of the present invention has a number average molecular weight of 10000 to 600000. When the number average molecular weight of the polymer is less than 10000 or greater than 600000, it is difficult to achieve a desirable biodegradability that satisfies the mechanical properties and non-irritancy required for the materials to be placed in a living body.

In the $A^1BA^2$-type polymer of the present invention, the segment B has a number average molecular weight of 8000 or more, preferably 8000 to 50000, more preferably 10000 to 40000, and most preferably 12000 to 30000, in order to balance the desired rate of degradation and the mechanical properties of the polymer in vivo. When the number average molecular weight of the segment B is less than 8000, desired properties may not be obtained. When the number average molecular weight of the segment B exceeds 50000, viscosity of PEG material products becomes high, making it difficult to handle the products during production.

In the A¹BA²-type polymer of the present invention, each of the segments A¹ and A² preferably has a number average molecular weight of 200 to 1 50000, more preferably 200 to 40000, and most preferably 500 to 1 0000, in order to balance the mechanical properties and the rate of degradation of the obtained polymer. The total number average molecular weight of the segments A¹ and A² is preferably in the range of 1000 to 300000, more preferably in the range of 2000 to 80000, and most preferably in the range of 4000 to 20000. When the total number average molecular weight of the segments A¹ and A2 is smaller than 1000, or larger than 300000, it is difficult to obtain a polymer with sufficient mechanical properties.

The number average molecular weight of each segment of the present invention can readily be adjusted by adjusting the molecular weights and the amounts of materials upon preparation of each segment.

The segment B, a constituent of the polymer of the present invention, is a hydrophilic segment composed of polyethylene glycol having the above-specified number average molecular weight.

The segment B may be a commercially available PEG that has a primary amino group at either terminus. Examples of the terminal amino groups include aminomethyl, aminoethyl, and aminopropyl groups.

The segment A¹ and the segment A², each of which is a constituent of the polymer of the present invention, are segments having modified amino acids that have hydrophobicity and may or may not be identical to one another. While each of the segments A¹ and A² is composed of at least one unit, it is preferred that each of the segments A¹ and A² be a poly(modified amino acid) composed only of a plurality of modified amino acid units to provide the resulting polymer with a desired biodegradability.

The term modified amino acid or poly(modified amino acid) may refer to an amino acid or a poly-amino acid with its functional groups such as a carboxyl group, an amino group, a hydroxyl group, and a thiol group protected by protecting groups for the synthesis of amino acid-N-carboxylic anhydrides (NCA) using the phosgene method.

The protecting group in the modified amino acid or poly(modified amino acid) may include, for example, benzyl, methyl, ethyl, n-propyl, isopropyl, and higher alkyl groups when the functional group to be protected in the amino acid molecule is a carboxyl group. The protecting group may include, for example, benzyloxycarbonyl, benzyl, and o-nitrophenylsulfenyl groups when the functional group to be protected is an amino group. The protecting group may include, for example, benzyl and acetyl groups when the functional group to be protected is a hydroxyl group. The protecting group may include, for example, a benzyl group when the functional group to be protected is a thiol group.

Preferred examples of the amino acids in the modified amino acid or poly(modified amino acid) may include alanine, leucine, lysine, or valine.

Preferred examples of the modified amino acids that compose the segment A¹ and segment A² may include γ-benzylglutamate (which may be referred to simply as BLG, hereinafter) represented by the formula (1) and β-benzylaspartate (which may be referred to simply as BLA, hereinafter) represented by the formula (2).

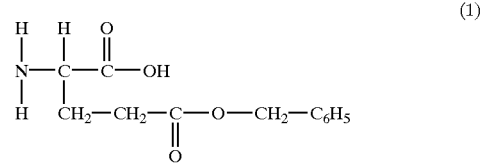

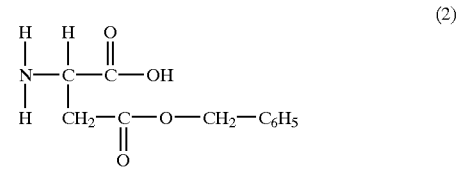

Preferably, the A¹BA² -type polymer of the present invention may be a tri-block copolymer as represented by the formula (3) especially when the polymer is applied in the fields where low irritancy to a living body is desired.

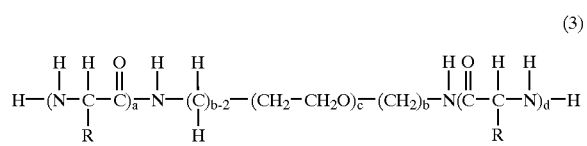

In the formula, the letters a and d each represent the number of repeats of the segments A¹ and A², respectively, and are each preferably an integer from 5 to 80. The letter b represents the number of repeats of methylene units in the region where the segment B is bonded to the segment A¹ or the segment A² and is preferably an integer from 1 to 10. A letter c represents the number of repeats of oxyethylene groups and is preferably an integer from 200 to 1200. R is preferably a unit depicted either as —$CH_2$—$CO_2$—$CH_2$-$CH_6H_5$ or —$CH_2$—$CH_2$—$CO_2$—$CH_2$—$C_6H_5$. Each R may or may not be identical to one another. The repeat numbers may be suitably adjusted to obtain the above-described number average molecular weights.

Preferably, the A¹BA²-type polymer of the present invention is a mixture of one or more types of the tri-block copolymers represented by the formula (3).

The polymer of the present invention may be produced through a suitable combination of known synthesis techniques. For example, the polymer of the present invention may be obtained by a ring-opening polymerization of the modified amino acid-N-carboxylic anhydrides (NCA) with the above-mentioned commercially available PEG having primary amino groups at both termini as a starting material.

In the polymerization reaction, at least one solvent selected from the group consisting of N,N-dimethylformamide (DMF), dimethyl sulfoxide (DMSO), N,N-dimethylacetoamide (DMAC), and 1,4-dioxane, or a mixed solvent of a solvent selected therefrom and dichloromethane or chloroform may be used.

Preferably, the ring-opening polymerization is carried out at a temperature of 20° C. to 50° C. for 6 to 36 hours.

This type of polymerization has long been known as the living anion polymerization, in which amino acids do not undergo racemization and polymers with relatively uniform molecular weights can be obtained.

A multiple-block copolymer can be synthesized by extending the chains of the tri-block copolymer that has the number average molecular weight of 10000 or less.

However, the multiple-block copolymerization requires chain-extending agents or catalysts. In such cases, tendency of the molecules to disperse becomes large, making it difficult to control the molecular weight and mechanical properties. Also, the presence of residual chain-extending agents or reaction catalysts often causes a problem. The polymer of the present invention can be produced without using such reaction catalysts or the chain-extending agents and, therefore, does not have problems associated with the use of these agents.

The biodegradable material of the present invention is the material containing the above-described polymer of the present invention and may be obtained by forming the polymers into desired shapes. For example, the polymer of the present invention may be dissolved in an organic solvent such as methylene chloride and/or chloroform and shaped into a sheet by casting or the like.

The biodegradable material thus obtained has a double-phase microstructure composed of modified amino acids or poly(modified amino acid) as the segments $A^1$ and $A^2$ and PEG as the segment B and exhibits a mechanical strength and rubber elasticity that are dependent upon the lengths of the block segments and the segment ratios.

The polymers in which the segments $A^1$ and $A^2$ are poly-β-benzyl-L-aspartate and/or poly-β-benzyl-L-glutamate exhibit particularly preferable biocompatibility and bioabsorbability since they are composed of PEG known as a low toxic and low stimulus polymer, and esters of an optically active amino acid and benzyl alcohol which is used as an additive of medications.

The rate of degradation in vivo of the biodegradable material of the present invention can be adjusted by suitably controlling the ratio of the hydrophobic segments $A^1$ and $A^2$ to the hydrophilic segment B in the polymer of the present invention used, with respect to number average molecular weight or molecular weight. When the polymer is shaped into a sheet, the rate of biodegradation can readily be adjusted by suitably controlling the dimensions, such as thickness, of the sheets.

The biodegradable material of the present invention may contain other polymers than the polymer of the present invention. Examples of such other polymers may include hyaluronic acid, collagen, polycaprolactone, polylactate, and carboxymethylcellulose.

The membrane for preventing tissue adhesion and artificial dura mater of the present invention may be obtained by shaping the polymer of the present invention into sheets by known methods for forming membranes. The rate of biodegradation of the membrane for preventing tissue adhesion and artificial dura mater can be suitably adjusted by adjusting molecular weights of the polymer of the present invention used and the ratio of the molecular weights of the segments or the thickness of the sheet. The suture thread of the present invention may be obtained by shaping the polymer of the present invention into fibers. The rate of degradation of the suture thread of the present invention can be suitably adjusted by adjusting the molecular weight of the polymer of the present invention used or the ratio of the molecular weights of the segments.

The implant preparation or sustained-release drug base of the present invention may be obtained by forming a hydrophobic drug and the polymer of the present invention into the forms of sheets or microgels. The rate of drug release may be controlled by suitably varying the total number average molecular weight of the polymer of the present invention and the average number molecular weights of the segment $A^1$ and segment $A^2$.

In cases of implant preparations, the polymer of the present invention may be shaped into the forms of hollow threads or tubes. Such implant preparations may be used in applications where the implant preparations are placed in a living body and then degrade in a sustained manner.

Since the polymer of the present invention has unique characteristics such as the ability to retain water, the ability to form a hydrogel, and the ability to hydrolyze in a living body, it can be widely applied to various products including toiletries and cosmetics, as well as the above-described applications.

Since the polymer of the present invention includes the hydrophobic segments $A^1$ and $A^2$ and the segment B of the hydrophilic PEG with a predetermined molecular weight and has a number average molecular weight of 10000 to 600000, the degradation rate can be adjusted by suitably selecting the molecular weights of the segments or the ratio of the molecular weights of the segments, while desired mechanical properties and non-irritancy are retained in a living body. Accordingly, the polymer of the present invention is suitable for use in biodegradable elements to be embedded in a living body such as membranes for preventing tissue adhesion, suture threads, implant preparations or sustained-release drug bases.

Also, when placed in water, the polymer of the present invention takes the form of hydrogel. The hydrogel has a sufficient flexibility. When the hydrogel is left in water as a swollen state at room temperature for a prolonged time, the hydrogel can retain the original shape that it assumes immediately after it has swollen in water. This preferred characteristic of the hydrogel makes the polymer of the present invention applicable in a wide variety of applications.

The biodegradable material of the present invention is particularly advantageous when it is used in the membrane to prevent tissue adhesion since it makes handling of the membrane easy while the membrane is being placed in tissue and provides the membrane with a high followability to follow soft tissue after it has become gel.

EXAMPLES

While the present invention will be described in further detail with reference to particular examples, the invention is not limited thereto. Methods and conditions of analyses are presented in the following.

<Methods for $^1$H-NMR Analysis>
Model: JNM EX-270 manufactured by NIHON DENSHI (JEOL) Ltd.
Solvent: DMSO-$d_6$,
Temperature for measurement: 80° C.,
Internal standard: DMSO
<Methods for Measurements of Molecular Weights Using GPC>
GPC model: SC-8020 system manufactured by TOSOH Co., Ltd.
Column: TSK gel G3000Hhr+G4000Hhr (two columns),
Eluent: DMF (containing 10 mM lithium chloride),
Flow rate: 0.8 ml/min,
Detection means: RI
Standard material: PEG
<Methods for Testing Biodegradability>

For testing biodegradability, square sample polymer sheets having side-length of 2 cm are implanted in abdominal cavities of male ddy mice, aged 8 weeks, through open abdominal surgery. After it is confirmed that the sheets have absorbed enough bodily fluids on the surfaces of tissue, adhered to the tissue, softened rapidly and started exhibiting the followability to the surrounding soft tissue, peritonea are closed by stitches. The mice, with the sheets implanted, are kept for the following 3 days. Three animals are then sacrificed each day and cut open to retrieve the implanted sheets. Dry weights of the sheets are measured. Differences between these measurements and the weights of the sheets prior to the placement in mice are taken as the results of the biodegradability tests.

<Methods for Adhesion Prevention Tests>

In adhesion prevention tests, iliac veins of 17 female Wistar rats are ligated at the proximal portion by 3-0 silk threads to stop the blood circulation and the veins are cut at about 1 mm downstream of the ligation. After a sample polymer sheet has been placed over the entire treatment site in each rat, peritoneum and then skin are closed by stitches. After one week, the rats are cut open to determine the occurrence of adhesion. The rate of adhesion prevention are measured based on the following equation:

Adhesion Prevention Ratio(%)=(The number of rats without adhesion)/(Total number of rats (=the number of rats with adhesion+the number of rats without adhesion))×100

<Tensile Strength Tests>

Obtained hydrogel was cut into strips of 2 mm wide and the strips were submerged in water until the test. Measurements were taken 5 times for each sample and the average was determined for three points. Also, the maximum load was determined by dividing the average of the three points by the cross-sectional area of the sample.

Example 1

Under a dry inert gas atmosphere, 1.0 g of PEG with aminopropyl groups attached to opposite termini (20000 g/mol) was dissolved in 7 ml of N,N-dimethylformamide (DMF) in an oil bath at 40° C. To this solution, 1.0 g of β-benzyl-L-aspartate-N-carboxylic anhydride (BLA-NCA) was added (80 equivalents for 1 mol of PEG). The reaction was allowed to proceed overnight, and the solution was then added dropwise to an ice-cooled diisopropyl ether to precipitate a white solid. The solid was vacuum-filtrated and was then dissolved in methylene chloride for repeated crystallization. After vacuum-drying, an $A^1BA^2$-type tri-block copolymer having the PBLA-PEG-PBLA structure was obtained.

Figure 2:
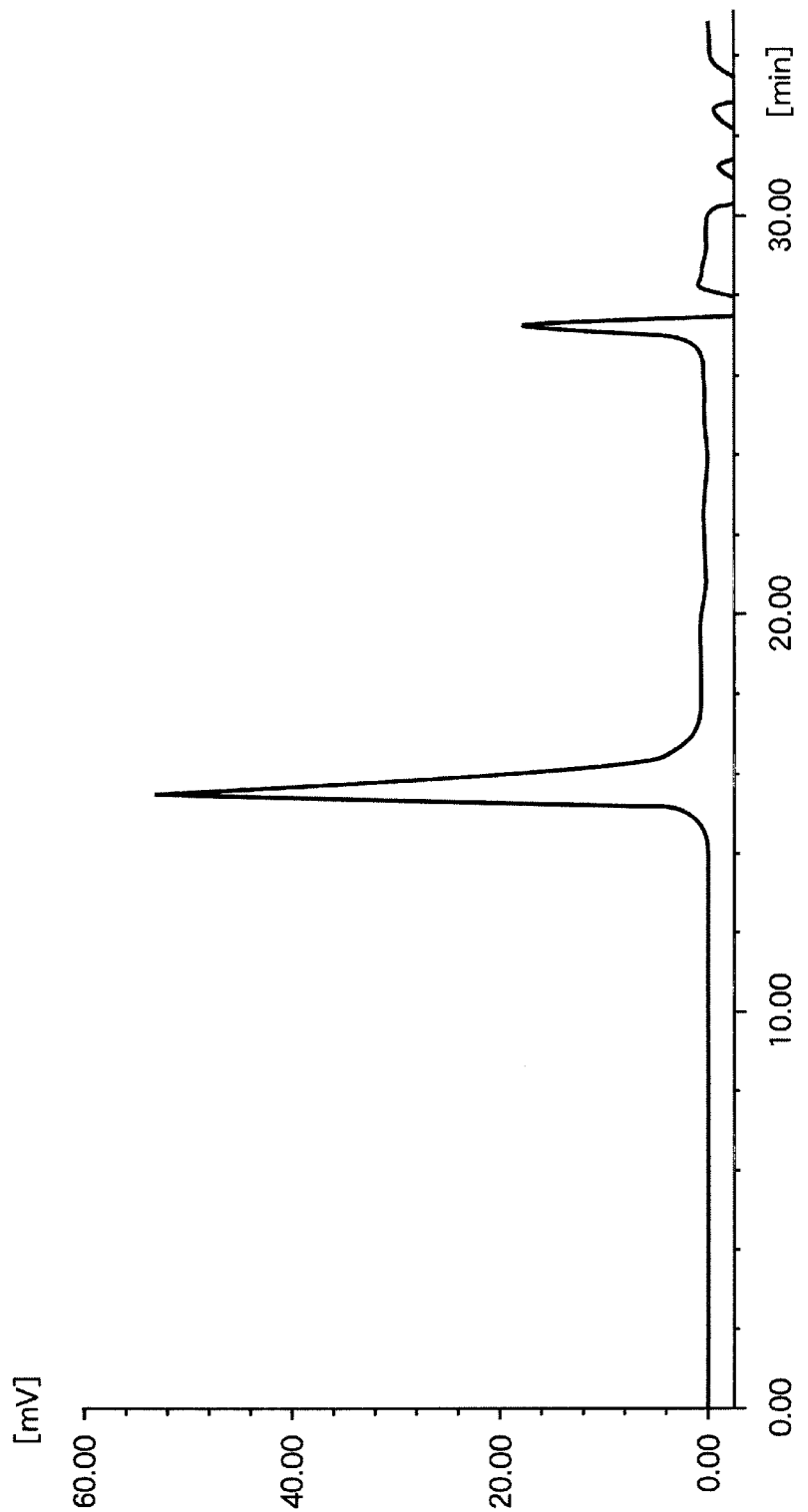
FIG. 2 shows a GPC spectrum of the tri-block copolymer synthesized in Example 1.

$^1$H-NMR of the resulting polymer were measured, as well as the number average molecular weight of the segment B, the total number average molecular weight of the segment $A^1$ and the segment $A^2$, and the number average molecular weight of the resulting polymer, through GPC analysis. The results are as shown in Table 1. Also, the results of $^1$H-NMR and the results of GPC analysis are shown in FIG. 1 and FIG. 2, respectively.

From the results of $^1$H-NMR, the integration ratio of methylene protons (1814H) of PEG at 3.7 ppm to aromatic protons at 7.5 ppm was determined to be to 36.3:5. From this integration ratio, the number of repeats of PBLA unit was calculated to be about 50 units. Also, from the results of the GPC analysis, it was determined that Mw/Mn=1.07 and the resulting polymer was relatively monodispersing.

Example 2

An $A^1BA^2$-type tri-block copolymer having the PBLA-PEG-PBLA structure was obtained in the same manner as in Example 1 except that the amount of BLA-NCA was 64 equivalents with respect to the amount of PEG. The same analyses as in Example 1 were conducted with the resulting polymer. The results are shown in Table 1. From the results of $^1$H-NMR, the integration ratio of methylene protons (1814H) of PEG at 3.7 ppm to aromatic protons at 7.5 ppm was determined to be 46.2:5. From this integration ratio, the number of repeats of PBLA unit was calculated to be about 40 units. Also, from the results of the GPC analysis, it was determined that Mw/Mn=1.07 and the resulting polymer was relatively monodispersing.

Example 3

An $A^1BA^2$-type tri-block copolymer having the PBLA-PEG-PBLA structure was obtained in the same manner as in Example 1 except that the amount of BLA-NCA was 100 equivalents with respect to the amount of PEG. The same analyses as in Example 1 were conducted with the resulting polymer. The results are shown in Table 1. From the results of $^1$H-NMR, the integration ratio of methylene protons (1814H) of PEG at 3.7 ppm to aromatic protons at 7.5 ppm was determined to be 29.5:5. From this integration ratio, the number of repeats of PBLA unit was calculated to be about 60 units. Also, from the results of the GPC analysis, it was determined that Mw/Mn=1.08 and the resulting polymer was relatively monodispersing.

Example 4

An $A^1BA^2$-type tri-block copolymer having the PBLG-PEG-PBLG structure was obtained in the same manner as in Example 1 except that γ-benzyl-L-glutamate-N-carboxylic anhydride (BLG-NCA) was used in place of BLA-NCA. The same analyses as in Example 1 were conducted with the resulting polymer. The results are shown in Table 1. From the results of $^1$H-NMR, the integration ratio of methylene protons (1814H) of PEG at 3.7 ppm to aromatic protons at 7.5 ppm was determined to be 89.5:5. From this integration ratio, the number of repeats of PBLG unit was calculated to be about 60 units. Also, from the results of the GPC analysis, it was determined that Mw/Mn=1.09 and the resulting polymer was relatively monodispersing.

Comparative Example 1

An $A^1BA^2$-type tri-block copolymer having the PBLA-PEG-PBLA structure was obtained in the same manner as in Example 1 except that PEG with a number average molecular weight of 4000 was used and the amount of BLA-NCA was 16 equivalents with respect to the amount of the PEG with the number average molecular weight of 4000. The same analyses as in Example 1 were conducted with the resulting polymer. The results are shown in Table 1. From the results of $^1$H-NMR, the integration ratio of methylene protons (1814H) of PEG at 3.7 ppm to aromatic protons at 7.5 ppm was determined to be 36.8:5. From this integration ratio, the number of repeats of PBLA unit was calculated to be about 10 units. Also, from the results of the GPC analysis, it was determined that Mw/Mn=1.06 and the resulting polymer was relatively monodispersing.

Comparative Example 2

Under a dry inert gas atmosphere, 2.0 g of PEG with aminopropyl groups attached to opposite ends (2000 g/mol) were dissolved in 10 ml of chloroform in an oil bath at 40° C. To this solution, 2.0 g of BLA-NCA were added (8 equivalents for 1 mol of PEG).

The reaction was allowed to proceed for 2 hours. 170 mg of hexamethylenediisocyanate (HDI) (1 equivalent for 1 mol of PEG) were then added to the solution. The reaction was allowed to proceed for another hour. The reaction mixture was then added dropwise to an ice-cooled diisopropyl ether to precipitate a white solid. The solid component was vacuum-filtrated and was then dissolved in methylene chloride for repeated crystallization. After vacuum operation, a multi-block copolymer including the PBLA-PEG-PBLA structure was obtained.

$^1$H-NMR of the resulting polymer was measured, as well as the number average molecular weight of the segment B, the total number average molecular weight of the segment A1 and the segment A2, and the number average molecular weight of the resulting polymer, through GPC analysis. The results are shown in Table 1.

Comparative Examples 3 and 4

A multiple-block copolymer including the PBLA-PEG-PBLA structure was obtained in the same manner as in Comparative Example 2 except that the amount of HDI was 12.8 g (0.75 equivalent for 1 mol of PEG) (Comparative Example 3) or 149 mg (0.875 equivalent for 1 mol of PEG) (Comparative Example 4).

$^1$H-NMR of the resulting polymer was measured, as well as the number average molecular weight of the segment B, the total number average molecular weight of the segment $A^1$ and the segment $A^2$, and the number average molecular weight of the resulting polymer, through GPC analysis. The results are shown in Table 1.

Comparative Example 5

Figure 3:
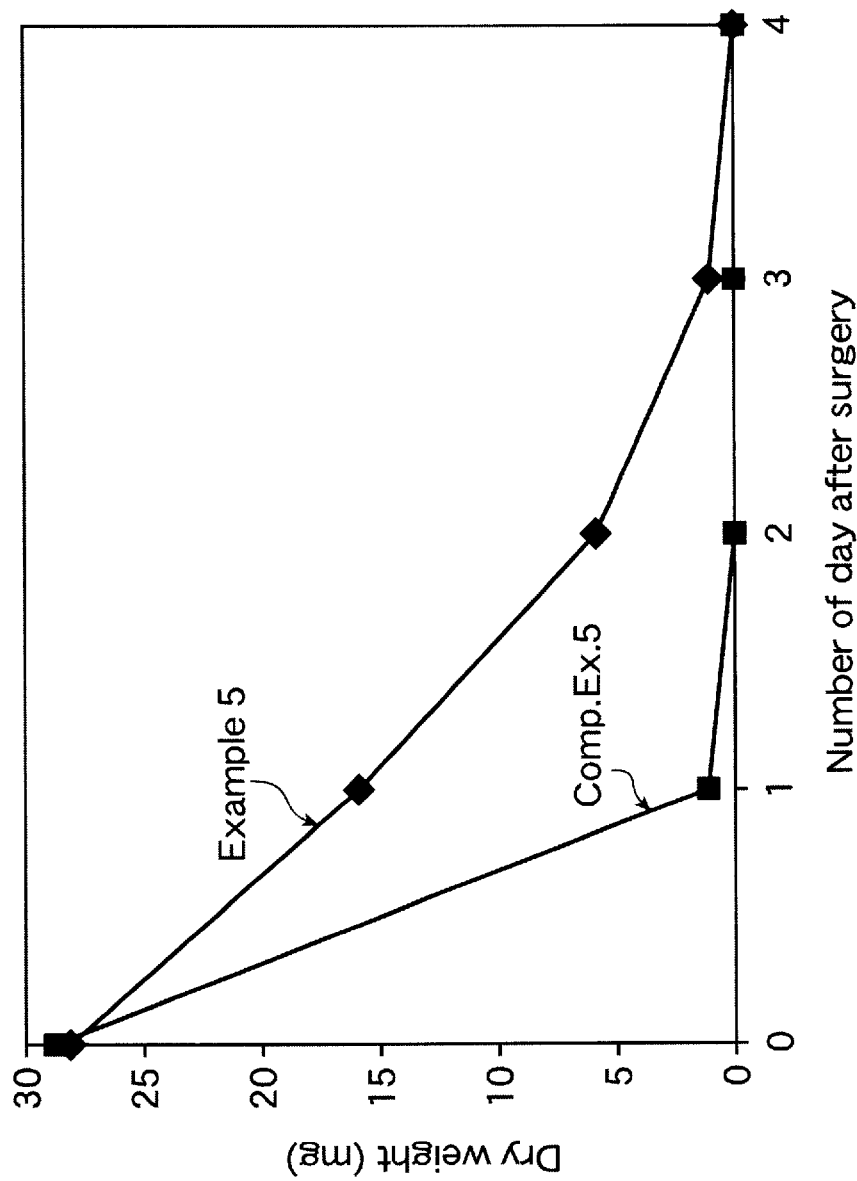
FIG. 3 is a graph showing the results of biodegradability tests conducted in Example 5 and Comparative Example 5.

Sheets were obtained in the same manner as in Example 5 except that tri-block copolymer with the number average molecular weight of 6000 that was synthesized in Comparative Example 1 was used. The resulting sheets were tested for the biodegradability in the same manner as in Example 5. The results are shown in FIG. 3. Further, the adhesion prevention tests were conducted with 14 mice. The results are shown in Table 2.

As can be seen from FIG. 3, the sheet obtained in Comparative Example 5, made of the tri-block copolymer with the number average molecular weight of 6000, degraded so fast that it substantially disappeared one day after the surgery. In contrast, the sheet obtained in Example 5, made of the tri-block copolymer with the number average molecular weight of 30000, degraded at an ideal rate.

In addition, the tri-block copolymers obtained in Examples 1 through 4, each of which contains PBLA or PBLG as a hydrophobic poly(modified amino acid), are water-soluble since they are hydrolyzed at benzyl esters. The sheets made of such tri-block copolymers will completely disappear within a few minutes when placed in an aqueous solution of sodium hydroxide since they are hydrolyzed at ester portions. These sheets are particularly advantageous in that they have no adverse effects on mice when placed in their abdominal cavities and have been completely degraded and disappeared when the mice are cut open three days after the placement.

TABLE 1

|  | Ex. 1 | Ex. 2 | Ex. 3 | Ex. 4 | Comp Ex. 1 | Comp. Ex. 2 | Comp. Ex. 3 | Comp. Ex. 4 |
| --- | --- | --- | --- | --- | --- | --- | --- | --- |
| Segment B MW | 20,000 | 20,000 | 20,000 | 20,000 | 4,000 | 2,000 | 2,000 | 2,000 |
| MW of segments $A^1 + A^2$ | 10,000 | 8,000 | 12,000 | 4,000 | 2,000 | 1,600 | 1,600 | 1,600 |
| Ratio of NMR integration | 36.3:5 | 46.5:5 | 29.5:5 | 89.5:5 | 36.8:5 | 22.8:5 | 22.5:5 | 22.7:5 |
| Calculated number of units $A^1 + A^2$ | 50 | 40 | 60 | 20 | 10 | 8 | 8 | 8 |
| Total MW | 30,000 | 28,000 | 32,000 | 24,000 | 6,000 | 33,000 | 21,000 | 25,500 |
| Dispersion ratio Mw/Mn | 1.07 | 1.07 | 1.08 | 1.09 | 1.06 | 1.31 | 1.33 | 1.41 |

Molecular weights are expressed in number average molecular weights.

Example 5

5 ml of methylene chloride were added to 500 mg of the tri-block copolymer synthesized in Example 1. The mixture was exposed to ultrasonic wave for 5 minutes to completely dissolve the polymer. The resulting polymer solution was poured into petri dishes of 60 mm in diameter, which were then left for 2 hours at room temperature to evaporate the solvent. The dishes were then dried in an incubator at 55° C. for 2 hours to obtain colorless, transparent sheets.

The sheets were placed in water and were allowed to swell to form colorless, transparent hydrogels. The hydrogels did not dissolve even after being left for more than three months at room temperature.

Using the sheets and hydrogels thus obtained, tests were conducted in the same manner as in the tests described above. The results of the biodegradability tests are shown in FIG. 3. The results of the adhesion prevention tests are shown in Table 2, and the results of the tensile strength tests are shown in Table 3.

Comparative Example 6

Using commercially available synthetic bioabsorbable adhesion prevention sheets (manufactured by Genzyme Co. Ltd.) containing sodium hyaluronate (hyaluronic acid Na) and carboxymethylcellulose (CMC) in a ratio of 2:1, the adhesion prevention tests were conducted with 11 rats. The results are shown in Table 2.

Comparative Example 7

Using commercially available synthetic bioabsorbable adhesion prevention sheets (manufactured by Johnson & Johnson. Co. Ltd.,) containing recycled oxidized cellulose, the adhesion prevention tests were conducted with 13 rats. The results are shown in Table 2.

TABLE 2

|  | Ex. 5 | Comp. Ex. 5 | Comp. Ex. 6 | Comp. Ex. 7 |
|---|---|---|---|---|
| Adhesion observed (number of animals) | 8 | 10 | 9 | 10 |
| No Adhesion (number of animals) | 9 | 4 | 2 | 3 |
| Number of animals tested | 17 | 14 | 11 | 13 |
| Adhesion prevention ratio (%) | 53 | 29 | 18 | 23 |

Example 6

Colorless, transparent sheets as well as hydrogels were prepared in the same manner as in Example 5, except that the tri-block copolymer synthesized in Example 2 was used in place of the tri-block copolymer synthesized in Example 1. The tensile strength tests were conducted with the resulting hydrogels in the same manner as in Example 5. The results are shown in Table 3.

Comparative Examples 8 to 10

Colorless, transparent sheets as well as hydrogels were prepared in the same manner as in Example 5, except that the multiple-block copolymer synthesized in Comparative Example 5 (Comparative Example 8), the multiple-block copolymer synthesized in Comparative Example 6 (Comparative Example 9), and the multiple-block copolymer synthesized in Comparative Example 7 (Comparative Example 10) were used in place of the tri-block copolymer synthesized in Example 1. The tensile strength tests were conducted with the resulting hydrogels in the same manner as in Example 5. The results are shown in Table 3.

TABLE 3

|  | Ex. 5 | Ex. 6 | Comp. Ex. 8 | Comp. Ex. 9 | Comp. Ex. 10 |
|---|---|---|---|---|---|
| Maximum load (gf/mm$^2$) | 125.9 | 89.3 | 47.6 | 73.2 | 65.1 |
| Elongation (%) | 282.0 | 225.2 | 91.22 | 132.4 | 131.6 |

From these results, the polymers of the present invention have proven to be materials that exhibit a suitable biodegradability in vivo. Further, the polymers of the present invention have proven to be advantageous in that they have no adverse effects on mice when placed in their abdominal cavities as a biodegradable material sheet and have been completely degraded and disappeared without causing adhesion when the mice are cut open three days after the placement. The polymers of the present invention also exhibit ideal mechanical properties. Consequently, it has been found that the polymer of the present invention is suitable for use in biodegradable materials or membranes for preventing tissue adhesion, or the like.

What is claimed is:

1. An $A^1BA^2$-type polymer having a number average molecular weight of 10000 to 600000, wherein the polymer is composed of a segment $A^1$ and a segment $A^2$ each including hydrophobic poly modified amino acids, and a segment B composed of polyethylene glycol with a number average molecular weight of 8000 or higher, the segment $A^1$ being bonded to one end of the segment B while the segment $A^2$ is bonded to the other end of the segment B, wherein the total number average molecular weight of the segment $A^1$ and the segment $A^2$ is from 4000 to 20000.

2. The polymer according to claim 1, wherein the segment $A^1$ and the segment $A^2$ is the same or different and the modified amino acids of each of the segments $A^1$ and $A^2$ are selected from the group consisting of poly-β-benzyl-L-aspartate, poly-γ-benzyl-L-glutamate, and a mixture thereof.

3. The polymer according to claim 1, wherein the polymer is an $A^1BA^2$-type triblock copolymer with each of the segment $A^1$ and the segment $A^2$ being a block segment.

4. A biodegradable material comprising the polymer of claim 1.

5. A membrane for preventing tissue adhesion consisting essentially of the biodegradable material of claim 4.

6. An artificial dura mater consisting essentially of the biodegradable material of claim 4.

7. A suture thread consisting essentially of the biodegradable material of claim 4.

8. An implant preparation consisting essentially of the biodegradable material of claim 4.

9. A sustained-release drug base consisting essentially of the biodegradable material of claim 4.

10. The polymer according to claim 2, wherein the ratio of the number of hydrogen atoms bound to aromatic rings in the segments of $A^1$ and $A^2$ with respect to the number of methylene hydrogen atoms in the segment B ranges from 5:29.5 to 5:89.5.

* * * * *

UNITED STATES PATENT AND TRADEMARK OFFICE
CERTIFICATE OF CORRECTION

PATENT NO.     : 6,673,361 B1
DATED          : January 6, 2004
INVENTOR(S)    : Atsuhiko Ogura et al.

It is certified that error appears in the above-identified patent and that said Letters Patent is hereby corrected as shown below:

<u>Title page,</u>
Item [75], Inventors, delete "Hiroshi Iwasaki, Iruma (Japan)" and substitute
-- Hiroshi Iwasaki, Kanagawa, (Japan) --.

Signed and Sealed this

Thirteenth Day of July, 2004

JON W. DUDAS
*Acting Director of the United States Patent and Trademark Office*